United States Patent [19]

Lekberg

[11] 4,052,451
[45] Oct. 4, 1977

[54] PREPARATION OF CALCIUM PANTOTHENATE

[76] Inventor: Robert D. Lekberg, 4040 W. 123rd St., Alsip, Ill. 60658

[21] Appl. No.: 666,040

[22] Filed: Mar. 11, 1976

[51] Int. Cl.$^2$ .................. C07C 99/04; C07C 99/10
[52] U.S. Cl. ..................... 260/534 A; 260/534 C
[58] Field of Search ................................. 260/534 A

[56] References Cited

U.S. PATENT DOCUMENTS

| 2,367,791 | 1/1945 | Parke et al. | 260/534 A |
| 2,441,949 | 5/1948 | Babcock | 260/534 A |
| 2,957,025 | 10/1968 | Brooks | 260/534 A |
| 3,935,256 | 1/1976 | Verbeeck | 260/534 A |

OTHER PUBLICATIONS

Morrison et al., Organic Chem., 3d ed. Allyn & Bacon, Inc., Boston, 588-589 (1974).
Wagner et al., Synthetic Org. Chem., John Wiley & Sons, Inc., New York, p. 412-415 (1965).
Stecher et al., Merck Index, 8th ed., Merch & Co., Rahway, N.Y., p. 858 (1968).

*Primary Examiner*—James O. Thomas, Jr.
*Assistant Examiner*—G.T. Breitenstein
*Attorney, Agent, or Firm*—Bruce K. Thomas; Paul L. Brown

[57] ABSTRACT

Beta-amino propionitrile is hydrolyzed with potassium hydroxide to produce potassium beta alanate, which, upon acidification produces free beta alanine with some potassium sulfate precipitate. The beta alanine solution with residual potassium sulfate is concentrated under vacuum to a thick syrup, shocked with an excess of a selected alcohol to produce a solid mass of beta alanine with the remaining theoretical potassium sulfate. The solid product is converted to calcium beta alanate under anhydrous conditions for reaction with racemic pantoyl lactone to form pure calcium pantothenate and allowing the entrained potassium sulfate to settle out. Contrary to expectations, under these conditions there was no double displacement and the presence of potassium sulfate did not interfere with the reaction.

10 Claims, No Drawings

PREPARATION OF CALCIUM PANTOTHENATE

BACKGROUND OF THE INVENTION

The fusion of calcium beta alanate with alpha-hydroxybeta, beta dimethyl-gamma-butyrolactone has been used to prepare calcium pantothenate. Another route is the reaction of beta-alanine with the lactone in aqueous calcium hydroxide. A direct fusion of the lactone with beta-alanine at about 150° C produces pantothenic acid, according to U.S. Pat. No. 2,418,902 but the temperature must not be allowed to reach 200° C because of decomposition detrimental to the purity of the end product. This reaction is only 17% complete. Also, the reaction of beta-alanine, calcium hydroxide and the lactone in an aliphatic alcohol solution is reported in British Pat. No. 561,877. Each of these processes require complicated purification procedures directed to the elimination of volatiles to prepare the dried salt. The British patent describes the preparation of crystalline calcium pantothenate by reaction of calcium metal with B-alanine in methanol solution to form solid calcium beta alanate for reaction with the lactone in isopropyl alchohol solution, the last step taking from 3 to 6 days.

U.S. Pat. No. 2,234,680 and 2,418,902 describe a more direct approach by reacting the lactone with beta alanine at about 178° C to produce pure pantothenic acid for conversion directly to the calcium salt which can be administered in such form without the need for purification. The use of calcium oxide in the final stages to produce calcium pantothenate from the reaction of equimolecular amounts of the butyrolactone and beta alanine in anhydrous alcohol, in the presence of a molecular equivalent of a secondary or tertiary amine, described in U.S. Pat. No. 2,496,363 is time consuming, requires charcoal filtering and final seeding to precipitate the final product. Furthermore, the reaction produces one equivalent of water which contaminates any recovered alcohol and amine, which for re-use must first be dehydrated and interferes with the preparation of a dried crystalline product.

U.S. Pat. No. 2,809,213 by the instant inventor, represents an improvement over the process of U.S. Pat. No. 2,234,680 in that calcium metal is used in place of the calcium oxide, thus allowing the preparation of either an optically active form of the salt or its corresponding optically inactive racemic form. By way of explanation, the presence of an asymmetric carbon atom in pantothenic acid explains the fact that in the stable salts thereof there exists two optically active forms, one dextro-rotatory and the other levo-rotatory. The dextro-rotatory form is the most important of these two forms because it is biologically active while the levo-rotatory form is to the contrary, biologically inactive. In addition, there exists a third or racemic form which is optically inactive but biologically active to the extent of approximately one-half that of the corresponding dextro-rotatory form.

While the dextro-rotatory form of calcium pantothenate has a biological potency equivalent to approximately twice the same amount of racemic calcium pantothenate, nevertheless, the cost of preparation per unit weight of biologically active mass is far greater for the dextro-rotatory form as compared with the racemic form. This is due to the fact that it is necessary to use the relatively expensive levo-rotatory alpha-hydroxy-beta, beta-dimethyl-gamma-butyrolactone in the preparation of dextro-rotatory pantothenic acid salts which lactone is obtained by preparing derivatives of the synthetically produced racemic form of the lactone with an optically active base such as an alkaloid, and resolving the optically active isomers therefrom.

SUMMARY OF THE INVENTION

Briefly the instant process is based on the discovery that the hydrolysis of beta-amino propionitrile with aqueous potassium hydroxide followed by sulfuric acid conversion of the potassium salt of beta alanine produces free beta alanine and insoluble potassium sulfate, the entrained portions of which, amounting to about 10% by weight, do not interfere with the subsequent conversion to calcium beta alanate, provided essentially anhydrous conditions are maintained. And, quite unexpectedly the presence of the potassium sulfate impurities does not interfere with the subsequent reaction of the pantoyl lactone to produce relatively pure calcium pantothenate (dl). Furthermore, the reactions are carried out using ordinary stainless steel or steel equipment, using inexpensive materials and no complicated purification or resin treatment steps are necessary.

An economical method for the preparation of calcium pantothenate is disclosed wherein beta-amino propionitrile is hydrolyzed with potassium hydroxide, and the aqueous salt solution is reacted with sulfuric acid to form free beta alanine. Some water is distilled off and a precipitate of potassium sulfate forms which is separated leaving the beta alanine solution containing a residual soluble amount of the theoretical portion of potassium sulfate which can be tolerated in the further reaction. Here beta alanine is shocked out with methanol and dried followed by reaction with calcium methoxide under anhydrous conditions, forming calcium beta alanate for further reaction with racemic pantoyl lactone to produce methanol soluble racemic calcium pantothenate readily allowing the entrained potassium sulfate to settle out and be separated. Distillation of all methanol solvent from the organic phase produces pure calcium pantothenate (dl). The organic phase, without distillation of methanol, is alternately complexed with calcium chloride, in which event the complex of racemic calcium pantothenate easily precipitates. It is thus unnecessary to purify the intermediate beta alanine in conducting the reaction and the difficult and costly process of removing alkali metal chlorides from the reaction mass by ion exchange is avoided while at the same time using simple procedures, inexpensive reactants and without the necessity of employing complicated apparatus.

In order to illustrate the invention, the following non-limiting examples are given:

EXAMPLE NO. 1

One quarter mole (22.5 gms.) of pure beta alanine was dissolved in 20.0 gms. of water in a beaker fitted with a stirrer and a solution of 0.25 mole (10.0 gms.) of sodium hydroxide dissolved in 10 cc of water was added at room temperature. The ingredients were mixed thoroughly in an attempt to form the sodium salt of the beta alanine. 0.25 mole or 26.0 gms. of 35% hydrochloric acid was added and agitation continued for a limited time to reversibly displace the sodium and determine if, at these concentrations, any sodium chloride would precipitate. The reaction mixture was homogeneous and no sodium chloride would precipitate. There was no phase separation on standing at room temperature for an extended period of time.

EXAMPLE NO. 2

The experiment of Example 1 was repeated using a more dilute solution of 0.25 mole (22.5 gms.) of beta alanine in 30.0 gms. of water and 0.25 mole (14.0 gms.) of potassium hydroxide dissolved in 20.0 gms. of water to form the potassium salt of beta alanine. In this instance 12.0 gms. of sulfuric acid in 20.0 gms. of water was added in an attempt to reversibly displace the potassium and precipitate it as potassium sulfate. At this concentration no potassium sulfate precipitated, nor did a precipitate form on standing at room temperature for an extended period of time.

EXAMPLE NO. 3

For the above reasons the experiment of Example 2 was repeated at greater concentrations, namely:

```
0.5 mole beta alanine (45.0 gms.)
40.0 gms. water
0.5 mole potassium hydroxide (28.0 gms.)
20.0 gms. water
24.0 gms. sulfuric acid (0.5 eq.)
20.0 gms. water
```

A precipitate of potassium sulfate was formed which upon filtration produced a net return of 49.3 gms. (weighed wet). The theoretical return of potassium sulfate is 45.0 gms. The filtrate, after concentration by heating, was shocked with methanol and 36.0 gms. of beta alanine returned as solids. The theoretical return of beta alanine is 45.0 gms. The beta alanine contained about 10% of inorganic potassium sulfate determined by ashing the beta alanine portion. No further returns of beta alanine were sought.

Examples 1, 2 and 3 were conducted to determine the solubility and chemical reversibility characteristics of the reactants and their products, that is, to see if any potassium sulfate could be made precipitate. It was demonstrated that a major part of potassium sulfate could in fact be removed and leave an amount of the sulfate in the filtrate which does not have to be further purified out. Under these circumstances, the conversion to the calcium salt for subsequent reaction with the lactone may be possible to produce an end product of 10% or less inorganic sulfate. Accordingly, a complete beta amino propionitrile hydrolysis appeared feasible using potassium hydroxide, as follows in Example 4.

EXAMPLE NO. 4

0.5 mole (35.0 gms.) of beta amino propionitrile was dissolved in 60.0 gms. of water in a vessel equipped with an agitator and a reflux condenser at room temperature. To this solution was added 0.5 mole (28.0 gms.) of potassium hydroxide dissolved in 50.0 gms. of water. The mixture was agitated and gradually heated to the boiling point for about 30 minutes. The ammonia produced was stripped off under vacuum and some volatiles were removed to concentrate the reactant solution slightly, prior to reacting with sulfuric acid. When the contents of the vessel had returned to a temperature of about 20° C, a solution of 24.0 gms. of concentrated sulfuric acid (0.5 eq.) in 20.0 gms. of water was added slowly while agitation was continued. A precipitate formed and the organic-water phase was decanted off. The precipitated potassium sulfate was washed with 25 cc of water mixed with 75 cc of methanol producing 34.0 gms. of potassium sulfate (weighed wet), and identified as such. The theoretical amount of potassium sulfate is 43.5 gms. The organic-water phase, the filtrate, was concentrated under vacuum to a thick mobile mass and drowned with methanol. A precipitate of 38.0 gms. of predominately beta alanine was obtained. The theoretical yield is 45.0 gms. This organic phase proved upon ignition to be 9% inorganic. The inorganic phase upon ignition was 2% organic, showing a minimum of loss under these relatively crude separation conditions with only one washing step. An acceptable commercial beta alanine of Japanese origin is 2% inorganic. However, this experiment established that it was possible to precipitate the potassium sulfate at these concentrations and obtain not only acceptable yields of the intermediate, but also fair purity.

EXAMPLE NO. 4a

The experiment of Example 4 was repeated by replacing the potassium hydroxide solution with 0.5 mole (20.0 gms.) of sodium hydroxide in 50.0 gms. of water. After the addition of the sulfuric acid solution, it was found to be impossible to remove sodium sulfate except by ion exchange ie passing the diluted solution through an ion exchange resin. The number of such filtration and re-concentrating steps required made this approach impractical.

EXAMPLE NO. 5

For the purpose of corroborating Example No. 4 the experiment was conducted again under more carefully controlled conditions using the following ingredients with an increase in quantities to produce more product:

```
1.0 mole beta amino propionitrile (70.0 gms.)
100 gms. water
1.0 mole potassium hydroxide (56.0 gms.)
100 gms. water
1.0 mole sulfuric acid (48.0 gms.)
50 gms. water
```

The beta amine propionitrile and potassium hydroxide solutions were placed in a vessel equipped with an agitator and the hydrolysis was begun. The reaction mass was concentrated under 20 mm. vacuum at 44° C to remove all remaining ammonia. When 60 cc of water had been distilled off, the temperature had risen to about 54° C. The distilland was cooled to room temperature and the above cool sulfuric acid solution was added producing a ph of 8.50 and potassium sulfate precipitated. The supernatant organic-water phase was decanted from the inorganic potassium sulfate precipitate and the latter was washed with a solution containing 25 cc of water and 75 cc of methanol. The inorganic solids showed a return of 68.0 gms. of potassium sulfate. The theoretical return is 87.0 gms. However, this inorganic phase showed no loss on ignition. The wash fluids were combined with the organic-water phase. This organic-water phase was then concentrated by distilling off the water under vacuum at 49° C. A total of 58 cc of water was so removed.

The organic precipitate, formed by shocking with 400.0 ml of methanol, showed a return of 71.2 gms. of beta alanine in the first crop, which on ashing was 10% inorganic. The organic phase was distilled at atmospheric pressure to 75° C and vacuum stripped to remove the remaining methanol and re-shocked with methanol to produce 18.3 gms. of solids comprising a beta alanine-potassium sulfate mixture, as the second crop. The first crop of 71.2 gms. (less 10%) was 64.1 gms. of organic material. The ashed solids from the second crop were 10% inorganic. The second crop of 18.3 gms. (less 10%) was 16.5 gms. of organic material. The methanol filtrate from the second crop was distilled to 73° C at atmospheric pressure and then finished to a thick fluid under vacuum, producing a third crop of 1.9 gms. which was 1.7 gms. of organic material. The third crop was also approximately 10% inorganic. Thus a total return of 82.3 gms. of the free beta alanine was produced. The theoretical was 89.0 gms.

EXAMPLE NO. 6

To determine more about the nature of the reactions in the presence of known added potassium sulfate contamination, 350.0 gms. of methanol and 20.0 gms. of calcium metal were reacted for 1½ hours in a reflux vessel. 89.0 gms. of commercial Japanese beta alanine and 10 gms. of potassium sulfate (10% by wt.) were added to the vessel with agitation. 130 gms. (100% basis) pantoyl lactone (with 5% excess) having a methanol solution weight of 161 gms., were added and refluxed for 1½ hours. The refluxed reaction mass was decanted to leave a potassium sulfate precipitate amounting to 10.0 gms. of residue. 5.5 gms. of the precipitate was ashed to 5.2 gms. resulting in 5.4% organic or water. Separately, 80.0 gms. (about 40% excess) of calcium chloride was added to 300.0 gms. of anhydrous methanol and refluxed for 1½ hours, followed by cooling to room temperature. The decanted portion (after the separation of the potassium sulfate) was mixed with the cold calcium chloride-methanol solution and brought up to reflux for 2 hours. The product of the complex precipitate was filtered removing surplus calcium chloride, air-dried and 392.5 gms. of calcium chloride complex was obtained. The theoretical yield is 293.0 gms. of calcium pantothenate complex.

EXAMPLE NO. 7

As further confirmation of the ability to produce calcium pantothenate in the presence of entrained potassium sulfate using beta alanine produced in Example 5, Example No. 6 was repeated as follows:

Into a vessel equipped with an agitator and reflux condenser was placed 250.0 gms. of methanol and 10.0 gms. of calcium metal and the ingredients stirred and heated to a reflux temperature of about 73° C for about 1½ hours. The theoretical amount, 44.5 gms., plus 11% excess or approximately 50.0 gms. of potassium sulfate-contaminated beta alanine product from Example No. 5 was added followed by 65.0 gms., (100% basis) plus 5% excess or a total of 80.0 gms. of methanol solution of racemic pantoyl lactone, and refluxed for about 1½ hours.

The soluble racemic calcium pantothenate reaction mass was filtered leaving 4.2 gms. of potassium sulfate insolubles which exhibited 5% loss on ignition. The filtrate was allowed to cool. Separately 40.0 gms. of anhydrous (technical grade) calcium chloride was added to 200.0 gms. of methanol and refluxed for 1½ hours, followed by cooling to room temperature. The above previously decanted and cooled calcium pantothenate was next added to the cooled calcium chloride solution and refluxed for 1½ hours. The refluxed mass was filtered and air-dried, producing a dried residue weighing 146.8 gms. Further drying under vacuum at 80° C produced a residue of the complex of racemic calcium pantothenate weighing 127.2 gms. The theoretical yield was 146.5 gms. for an 88% yield.

Thus it is only necessary to know the organic percentage and then remove the excess entrained potassium sulfate after and when the beta alanine is a part of the methanol soluble dl calcium pantothenate molecule. The step of adding the calcium chloride is for the purpose of further purifying the calcium pantothenate after having removed the potassium sulfate. The complexed salt is a stable readily analyzable derivative. The excess of the lactone was used to insure the completion of the reaction and it proved to be unnecessary to use any excess beta alanine. Accordingly the beta alanine from the potassium hydroxide hydrolysis, need not be further purified and the initial potassium sulfate separation due to its insolubility at these concentrations was sufficient. Further concentration of the reaction mass by driving off the volatiles with heat, shocking the mass with methanol to produce free beta alanine for reaction with calcium methoxide followed by the lactone, still under anhydrous conditions, results in the soluble form of calcium pantothenate, leaving the remaining potassium sulfate to precipitate out. Accordingly in the presence of the reaction media, such as anhydrous methanol, the calcium and potassium did not double displace, as would be expected, producing calcium sulfate and potassium pantothenate. Since it is generally known that salts of beta alanine do not fully react with pantoyl lactone except under anhydrous conditions, advantage can be taken of this fact to produce good yields of high purity calcium pantothenate in spite of the presence of entrained amounts of potassium sulfate, found not to interfere with the reaction.

Other anhydrous low molecular weight aliphatic alcohols than methanol can be used, such as ethanol and isopropanol, in conducting the reaction. The word "shocked" as used herein means, in the trade, forced precipitation. The optically active and inactive forms of calcium pantothenate appear in about equal portions in the end product. About one-half of the racemic form of calcium pantothenate is dextro-rotary and it is essentially the only portion which is biologically useful. No attempts were made to produce a predominate amount of either isomer. The end uses as an animal food supplement are well known.

What is claimed is:

1. A process for the preparation of calcium pantothenate comprising:
   reacting beta-amino propionitrile with a substantially stoichiometric quantity of potassium hydroxide in aqueous media to produce potassium beta alanate;
   distilling off volatiles produced in the reaction;
   reacting the potassium beta alanate distilland with sulfuric acid to form free beta alanine and a precipitate of potassium sulfate;
   separating the precipitated potassium sulfate and recovering the filtrate;
   distilling the filtrate to remove water and recovering a concentrated filtrate;
   treating the concentrated filtrate with low molecular weight anhydrous aliphatic alcohol to form a precipitate comprising a mixture of beta-alanine and entrained potassium sulfate;
   reacting the beta-alanine and potassium sulfate mixture with calcium methoxide under substantially anhydrous conditions to form calcium beta alanate;
   reacting the calcium beta alanate with racemic pantoyl lactone in the presence of the entrained potassium sulfate under substantially anhydrous conditions to form substantially pure calcium pantothenate; and separating soluble calcium pantothenate from the remaining potassium sulfate which settles therefrom.

2. A process in accordance with claim 1 in which:
not less than a stoichiometric amount of sulfuric acid is used.

3. A process in accordance with claim 1 in which:
the calcium pantothenate is complexed with calcium chloride by initial reaction therewith in the presence of anhydrous methanol at room temperature and completion of the reaction at reflux temperature.

4. A process in accordance with claim 1 in which:
the calcium pantothenate is a dextro-levo mixture.

5. A process in accordance with claim 1 in which:
the calcium pantothenate is of the racemic form.

6. A process in accordance with claim 3 in which:
the calcium chloride complex of calcium pantothenate is a dextro-levo mixture.

7. A process in accordance with claim 3 in which:
the calcium chloride complex is of the racemic form.

8. A process for the preparation of calcium pantothenate comprising the steps of:
reacting beta-amino propionitrile with potassium hydroxide in aqueous media to form potassium beta alanate;

distilling off volatiles produced in the reaction;

reacting the potassium beta alanate distilland so produced with sulfuric acid in a minimum amount of water to form free beta-alanine and a precipitate of potassium sulfate;

separating the precipitated potassium sulfate and recovering the filtrate;

distilling the filtrate to remove water and recovering a concentrated filtrate;

treating the concentrated filtrate with an aliphatic alcohol under anhydrous conditions to form a mixture of precipitated beta-alanine and entrained potassium sulfate;

reacting the beta-alanine and potassium sulfate mixture with calcium methoxide to form calcium beta alanate;

reacting the calcium beta alanate with pantoyl lactone in the presence of the entrained potassium sulfate under substantially anhydrous conditions to form substantially pure calcium pantothenate; and separating soluble calcium pantothenate from the insoluble entrained potassium sulfate.

9. A process in accordance with claim 8 in which:
substantially equi-molar quantities of potassium hydroxide and beta amino propionitrile are reacted in the first step.

10. A process in accordance with claim 8 in which:
the calcium pantothenate formed is a mixture of the dextro-levo and racemic forms.

* * * * *